United States Patent [19]
Petolino

[11] Patent Number: 5,306,864
[45] Date of Patent: Apr. 26, 1994

[54] INCREASING THE ANTHER CULTURABILITY OF MAIZE

[75] Inventor: Joseph F. Petolino, Urbana, Ill.

[73] Assignee: United AgriSeeds, Savoy, Ill.

[21] Appl. No.: 839,024

[22] Filed: Feb. 18, 1992

Related U.S. Application Data

[63] Continuation of Ser. No. 657,884, Feb. 19, 1991, abandoned, which is a continuation of Ser. No. 279,467, Dec. 2, 1988, abandoned.

[51] Int. Cl.$^5$ .......................... A01H 5/00; A01H 4/00; A01H 1/04
[52] U.S. Cl. ..................................... 800/230; 800/235; 800/DIG. 56; 435/240.45; 435/240.49; 435/240.5
[58] Field of Search ........... 435/240.4, 240.45, 240.49; 800/200, 205, 230; 47/58.03, 58.05

[56] References Cited

PUBLICATIONS

Soller et al. (1983) TAG. vol. 67, pp. 25–33.
Dieu et al. (1986) Maydica 31(3) pp. 245–259.
Petolino et al. (1986) Crop Science vol. 26. pp. 1072–1074.
Poehlman (1987) *Breeding Field Crops* pp. 460–461.
Hoffman et al. (1982) TA6. vol. 61, pp. 225–232.

*Primary Examiner*—Gary Benzion
*Attorney, Agent, or Firm*—Kenneth L. Loertscher; Andrea T. Borucki

[57] ABSTRACT

This invention provides a process for producing germplasm of plant species exhibiting enhanced response to anther culture. The anther culture procedure itself is used as a selection criterion for genes favoring in vitro androgenesis. After subjecting anthers to standard anther culture regeneration procedures, the regenerated plants are intermated and self-pollinated to generate valuable genetic variability for improved culture response. The transfer of increased anther culturability to other selected germplasm is also possible.

9 Claims, 2 Drawing Sheets

INCREASING THE ANTHER CULTURABILITY OF MAIZE

This is a continuation of application Ser. No. 07/657,884, filed Feb. 19, 1991 now abandoned which is a continuation of application Ser. No. 279,467 filed Dec. 2, 1988, now abandoned.

TECHNICAL FIELD

This invention relates to a method of producing novel germplasm of plants capable of high levels of haploid and/or double haploid formation from cultured anthers and/or microspores.

BACKGROUND OF INVENTION

It is of great agricultural and economic interest to provide new plants which display an improvement in particular characteristics. Through proper breeding techniques, these characteristics can be introduced into new or existing genotypes of plant species which can then be marketed directly or used to produce superior hybrid plants.

The development of a hybrid variety conventionally involves three steps: (1) the selection of superior plants from various germplasm pools; (2) the selfing of the superior plants for several generations to produce a series of inbred lines, which although different from each other, breed true and are highly uniform; and (3) the crossing of selected inbred lines with unrelated inbred lines to produce the hybrid progeny ($F_1$). An important consequence of the homozygosity and homogeneity of the inbred lines is that the hybrid between any two inbreds will always be the same. Once the inbreds that give the best hybrid have been identified, the hybrid seed can be reproduced indefinitely as long as the homogeneity of the inbred parent is maintained.

There has been much discussion about the potential utilization of haploids in plant breeding. Since plant breeding is concerned with the development of genotypes to use directly or as parents of productive hybrids, the rapid advance to homozygosity which accompanies the doubling of haploids is an attractive feature. However, attempts at utilizing haploids in plant breeding have been frustrated by the lack of a reliable means of generating sufficient numbers of doubled haploid lines from a broad spectrum of commercially-important germplasm.

Anther culture provides a rapid method of inducing homozygosity in plants which are of interest for the production of breeding lines. Anther culture involves isolating immature anthers from plants and placing them onto a medium which induces the cells within the anther, which would normally be destined to become pollen grains, to begin dividing and form a cell culture from which plants can be regenerated. For a general discussion of anther culture, see J. M. Dunwell, "*Anther and Ovary Culture*", In S. W. J. Bright and M. G. K. Jones, (eds.), *Cereal Tissue and Cell Culture*, Martinus Nijhoff Publisher, 1985, Dordrecht, pp. 1–44. This process is known as androgenesis. The resulting cultures are haploid and contain only a single set of chromosomes from the original plants. The plants derived from these cultures are sterile unless chromosome doubling occurs, either spontaneously or by induction, to create doubled haploids which are fully fertile and completely inbred. Therefore, anther culture represents a potentially powerful method of rapidly producing large numbers of inbred lines for commercial evaluation.

Numerous studies on the in vitro culture of gametophytic cells with the aim of producing haploid plants have been reported during the last two decades. A large number of reviews, book chapters and symposia proceedings have been published as well (see generally Chu, "*Haploids in Plant Improvement*", In I. K. Vasil, W. R. Scowcroft, K. J. Frey (eds.), *Plant Improvement and Somatic Cell Genetics*, New York: Academic Press, 1982, pp. 129–158; Heberle-Bors, "*In Vitro Haploid Formation of Pollen: A Critical Review*", Theor. Appl. Genet. 71:361–374, 1985; and Hu and Yang, "*Haploids of Higher Plants in Vitro.*" Berlin, Heidelberg, Springer-Verlag, (1986)).

Anther culture represents a method by which, theoretically, large numbers of haploid individuals can be produced directly from anthers and/or microspores in vitro. (see Keller et al. "*Haploids from gametophytic cells —recent developments and future prospects*", In C. E. Green, D. A. Somers, W. P. Hackett, D. D. Biesoer (eds.), *Plant Tissue and Cell Culture*, Alan R Liss, New York, pp 223–241). Haploids can be regenerated from both male and female gametophytic cells through the culture of anthers, microspores, ovaries and ovules. A positive in vitro response will lead to the development of embryos and/or callus from which plants can be regenerated. Early events during in vitro culture have been characterized at the cytological, ultrastructural and biochemical level (Chen et al., "*Segmentation Patterns and Mechanisms of Genome Multiplication in Cultured Microspores of Barley*", J. Can, Genet. Cytol., 26:475–483 (1984); Raghavan, *Protein Synthetic Activity during Normal Pollen Development and During Induced Pollen Embryogenesis in Hyoscyamus niger*", J. Can Bot., 1984, 62:2493–2513; Huang, "*Ultrastructural Aspects of Pollen Embryogenesis in Hordeum, Triticum and Paeonia*", 1986).

Anther culture has been employed to obtain microspore-derived callus, embryos and plants in well over 200 species (Maheshwari et al., "Haploids from Pollen Grains-Retrospect and Prospect", Amer. J. Bot., 1982, 69:865–879). However, the anther culture responsiveness varies considerably among species. A comparison of the overall responsiveness of anther culturability is made difficult, as the results reported in published studies are given in different bases. For example, anther culturability has been defined by the induction of microspores that begin dividing, the number of embryos and-/or callus per anther, the percentage of anthers producing at least one embryo and/or callus, the number of haploid plants regenerated, and the number of dihaploid plants recovered.

The highest yield of responding anthers (anthers forming embryos and/or callus per 100 anthers plated) was found to be 87 percent in wheat (A. M. Wei, "*Pollen Callus Culture in Triticumaertivum*", Theor. Appl. Genet., 63, 1982, pp. 71–73), 67 percent in rice (S. L. Lin and H. S. Tsay, 1983, J. Agr. Res., China, cited in Dunwell, 1985), 17 percent in maize (Ting et al., "*Improved Anther Culture of Maize*" (Zea mays L.), Plant Science Lett., 23, 1981, pp. 139–145) and 1 percent in barley (Z. H. Xu and N. Sunderland, "*Innoculation Density in the Culture of Barley Anthers*", Scient. Sinic., 25, 1982, pp. 961–968). In rye, 43 developing structures per 100 anthers were observed (G. Wenzel et al., "*Increased Induction and Chromosome Doubling of Androgenetic Haploid Rye*", Theor. Appl. Genet., 51, 1977, pp. 81–86). Concerning plant regeneration, Petolino and Jones (J. F. Petolino and A. M. Jones, "*Anther Culture of Elite Genotypes of Maize*", Crop Science, 26, 1986, pp. 1072–1074) describe for maize that from 234 embryoids (from different genotypes) transferred to regeneration medium, 43 developed into plants. Frequencies of calli producing green plant per 100 cultured anthers are in wheat 72 percent (J. W. Ouyang et al., "*The Response of Anther Culture to Temperature in Triticum Aestivum*", Theor. Appl. Genet., 66, 1983, PP. 101–109), in rice 12 percent (L. J. Chen et al., "*Medium Evaluation for Rice Anther Culture*", in A. Fujiwara (ed.), "*Plant Tissue Culture*", pp. 551–551. Jap. Assoc. Plant Tissue Culture Tokyo, 1982) and in barley 10 percent (K. N. Kao, "*Plant Formation from Barley Anther Cultures with Ficoll Media*", Z. Pflanzenzuchtg., 103, 1981, pp. 437–443).

Although relatively rapid progress has been made in several species, many species of plants, unfortunately, have not shown detectable or significant anther culturability. Production of positive results in maize anther culture has been particularly slow (Nitsch et al., "*Production of Haploid Plants Zea mays and Pennisetum through Androgenesis*", In E. D. Earle, Y. Demarley (eds.) *Variability in Plants Regenerated from Tissue Culture*, Prager Publishers, New York, 1982, pp. 69–91). Response frequencies in cultured maize anthers have been very low in all but a few genotypes (see Ku et al. , "*Induction Factors and Morpho-cytological Characteristics of Pollen-derived Plants in Maize*", (Zea mays L. Proc Symp Plant Tissue Cult., (1978) Science Press, Peking, pp 35–42; Genovesi et al. , "*In vitro Production of Haploid Plants of Corn via Anther Culture*", Crop Science, 22, 1982, pp. 1137–1144, Dieu and Beckert, 1986; and Petolino et al., "*Anther Culture of Elite Genotypes of Maize*", Crop Science, 26, 1986, pp. 1072–1074).

Maize genotypes differ with respect to their amenability to anther culture (Petolino et al., 1986, supra) suggesting that genetic factors are important in determining the level haploid production. For anther culture-derived lines to be utilized in commercial maize breeding, commercially-acceptable germplasm will require increased responsiveness to anther culture. Specifically, any attempt to use anther culture in commercial breeding will require a considerable improvement in the overall efficiency of doubled haploid seed recovery. Generally, the major problems in the use of anther culture have been the relatively low response frequencies and the difficulties associated with plant regeneration and chromosome doubling in all but a few genotypes.

As can be seen from the above discussion, anther culture techniques are still rather empirical, and as such it is difficult to draw generalizations from the prior art.

It is thus an object of the invention to provide process for producing germplasm exhibiting enhanced response to anther culture.

It is an object of the invention to provide anther-derived, plants and seed.

Finally, it is an object of the invention to transfer the germplasm providing increased anther culturability from at least one plant in a species to other plants in the species.

SUMMARY OF THE INVENTION

In one embodiment, the present invention is a method for the production of a plant having improved anther culturability, the steps of the method comprising (1) providing anthers from at least one heterozygous donor plant; (2) regenerating, from the anthers obtained from the donor plant, at least two microspore-derived plants capable of being intermated; (3) intermating the regenerated plants to produce an F, population; and (4) self-pollinating or cross-pollinating individuals of the $F_1$ population to generate at least one $F_2$ population.

In another embodiment, this invention is an $F_2$ plant, or progeny thereof, said plant containing a HAC genetic factor, whereby the plant contains an anther culture response frequency of at least 10 percent greater than the anther response frequency of the original donor plant.

Figure 1A:
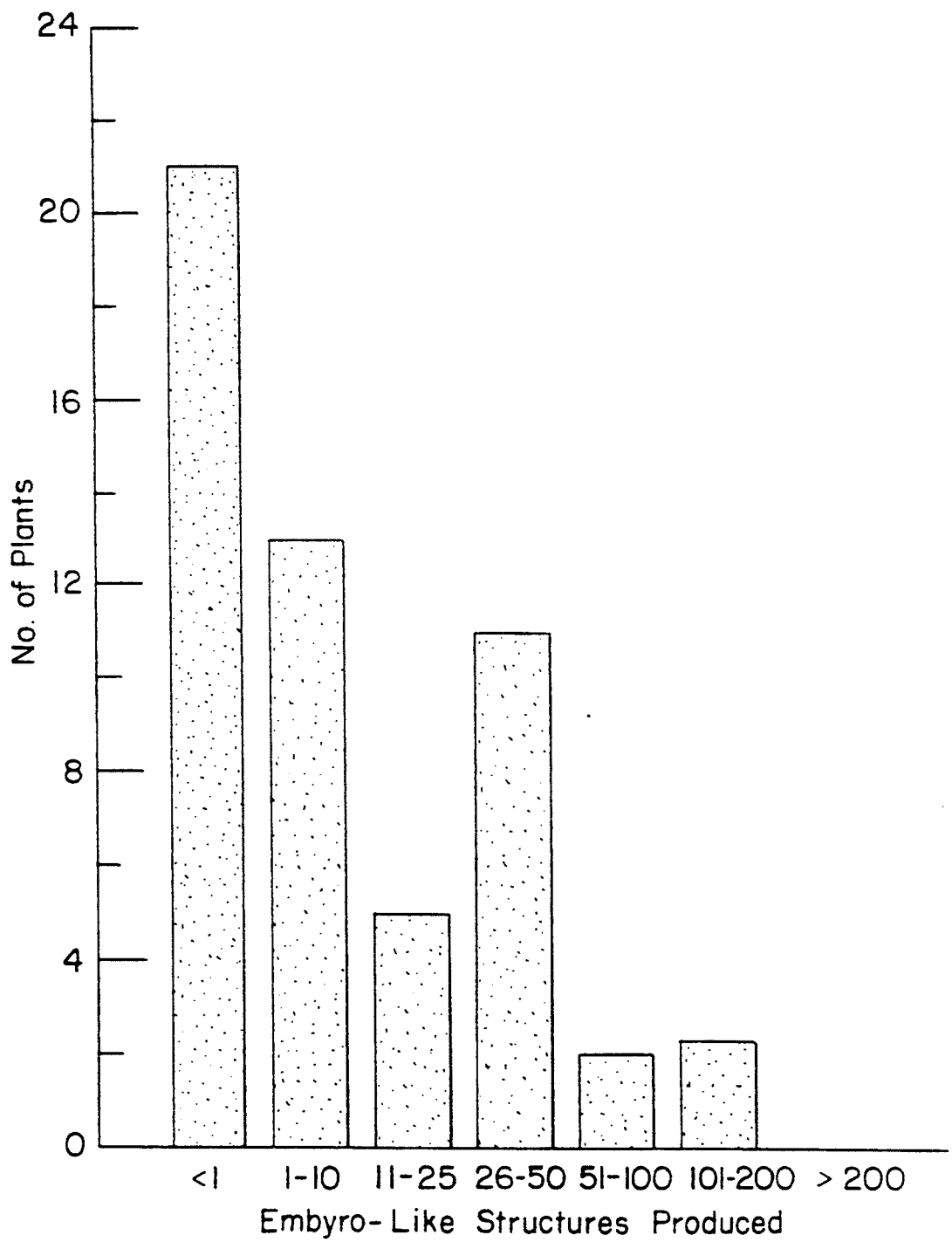
FIG. 1A illustrates the frequency distribution of anther culture response from individual maize plants: (H99×FR16) ×Pa91 Cn =53); * donor plants from which 190 39 and #139 were regenerated.

As used herein the term "plant" includes seed capable of being germinated into a plant; plant cells; ant protoplasts; plant cell or tissue cultures from which a plant can be regenerated; plant calli; plant clumps; and plant cells that are intact in a plant or parts of a plant, such as flowers, kernels, ears, cobs, leaves, husks, stalks, and the like.

The present invention is applicable to any plant species which may be anther cultured. The term plant "species" is meant to include monocotyledons (e.g., the grasses, and the cereal crops such as maize, rye, barley, wheat, sorghum, oats, millet and rice); and the dicotyledons (e.g., broad-leafed plants such as tobacco, potato and alfalfa). The monocotyledons are preferred because plant regeneration is not as well documented as for many dicotyledons. Because of its commercial importance, maize is particularly preferred for use in the present invention due to its heretofore reticence to anther culture.

Regardless of the previously attained anther frequency response of the species, the present method will provide an enhancement in anther frequency response in the regenerated $F_2$ progeny of at least 10 percent greater than the anther frequency response in either parent. Thus, for species which have demonstrated anther culturability at a relatively high level, this method will further enhance anther culturability in such species. More importantly, for species which have demonstrated the ability to be anther cultured, but at relatively low levels (e.g., maize), the present invention allows such species to now be anther cultured at perhaps significant levels. In maize, the anther culture response of the $F_2$ population will preferably be at least about 18 embryo-like structures per 100 anthers cultured (ELS/anthers), and most preferably at least about 30 ELS/anthers.

By "embryo-like structures" is meant globular masses of cells resulting from repeated divisions of microspores which are capable of continued growth and development.

CREATION OF GENOTYPE

Plants containing heterozygous genotypes may be obtained from any convenient source known to the skilled artisan. For example, the plants may be naturally heterozygous, occurring from open pollination; wild relatives of inbred lines; mutations of inbred lines; transformed inbred lines; and the progeny of crosses of inbred lines, each of which may have one or more desirable characteristics lacked by the other or which complement the other. Exemplary crosses include single crosses (i.e., two inbred lines are crossed to produce $F_1$ progeny), three-way crosses (i.e., three inbreds lines are crossed: $((A \times B) \times C)$), and double crosses (i.e., four inbred lines are crossed: $(A \times B) \times (C \times D)$).

Plant breeding techniques suitable for production of such first generation hybrids are well-known to those skilled in the art. Such techniques are described in "*Corn and Corn Improvement*", Sprague ed., *American Society of Agronomy*, Publication No. 18, Madison, Wis. (1977); Poelhman, J. H., "*Breeding Field Crop's*, Henry Holt and Company, New York, (1959); and in Welsh, J. R., "*Fundamentals of Plant Genetics and Breeding*", Wiley (1981). The disclosures of these volumes are herein incorporated by reference.

Preferably, at least one of the parents contains commercially-important traits. Although the anther culturability phenotype may be transferred to commercially-important plants, as discussed below, it is more convenient to utilize commercially-important plants directly in the method of the present method. The presence of other traits should be selected so as not to affect the transfer of genetic factors which express an anther culture phenotype. However, as discussed infra, the anther culture trait may subsequently be transferred from highly anther culture responsive plants to other plants, such as commercially-important plants.

A particularly preferred selection of plants is derived from maize plants made by a three-way cross of H99, FR16, and Pa91: (H99 $\times$ FR16) $\times$ Pa91. Seed for producing the inbred plants was obtained from Holden's Foundation Seeds, Williamsburg, Iowa, (H99 and Pa91) and Illinois Foundation Seed, Tolono, Ill. (FR16).

ANTHER CULTURE OF THE DONOR PLANT

The anthers may be removed from the plant at any suitable stage of maturity for anther culture. The stage of maturity will depend upon the particular species. Generally, the anthers will be removed when they contain microspores at the early uninucleate-late binucleate stage of development. Preferably, maize anthers are removed from the plant at between the late uninucleate-early binucleate stage of development.

Maturity of the anthers is determined microscopically by periodic sampling of plants. Microscopic techniques are well-known in the art. Generally, the stage of anther development is readily determined microscopically after treatment with nuclear staining; examples of suitable stains include acetocarmine and mithramycin.

After anthers from the donor plant have been isolated, the second step involves utilizing cell culture technology to isolate and characterize cell lines which express anther culturability. The anthers may be cultured by any standard technique which provides double haploid plants. The anther culture technique employed will of course depend upon the particular species used. For a general discussion of anther culture procedures see Dunwell (1985), supra; Keller et al. (1987), supra; and Bajaj, Y. P. S., "*In vitro Production of Haploids*", In Evans D. A., Sharp W. R., Ammirato P. V., Yamada Y. (eds.), *Handbook of Plant Cell Culture*, vol. 1, Macmillan, New York, 1983, pp 228-287.

INTERMATING OF REGENERATED PLANTS

After producing a population of regenerated double haploid plants as discussed above, the artisan should randomly cross the regenerated plants to produce a series of $F_1$ hybrids, and then self pollinate the $F_1$ hybrids to produce an $F_2$ population having genetic variability, i.e, segregating populations. The inventor has found, quite surprisingly, that by intermating regenerated plants of anther culture to produce an $F_1$ population and self-pollinating individuals of the $F_1$ populations to generate an $F_2$ population, the $F_2$ progeny of those plants have an anther response frequency at least 10 percent greater than the anther culture response of the donor plant.

Exemplary techniques for intermating the regenerated plants include single, three-way and double crosses of the regenerated population; the techniques for performing the crosses has hereinbefore been described and incorporated by reference. Preferably, the individuals of the regenerated population should be crossed in as many ways as possible in order to create several $F_2$ populations.

Intermating of the regenerated plants is followed by creating a segregating population to produce maximum genetic variability in the $F_2$ ($S_0$) populations. The $F_2$ population is created by self-pollinating or cross-pollinating individuals of the $F_1$ population. Any method of creating a segregating population to produce maximum genetic variability may be employed to create the $F_2$ population. Thus, the present invention contemplates pollinating individuals of the $F_1$ population by self pollination; or by being crossed with other plants such as with other members of the $F_1$ population, or even non-responsive plants; provided that the $F_2$ progeny of those plants have an anther response frequency at least 10 percent greater than the anther culture response of the donor plant. Self-pollination of the $F_1$ individuals is preferred maximize the release genetic variability of the $F_1$.

An exemplary method for maintaining a segregating population is as follows: about at least 50 seeds are planted and the resulting individuals are intermated (using each plant as a male and female once). See A. R. Hallauer, "*Principles of Cultivar Development*", in W. R. Fehr et al. (ed.), *Crop Species*, Macmillan Publishing Company, Vol. 2, 1987, Chapter 8 "Maize", 249-294. At least 25 ears from different plants should be harvested, the seed removed and mixed together. From this bulked seed mix, a random sample of seeds can be saved.

GENETIC FIXATION OF SEGREGATING POPULATION

Thereafter, the segregating populations are genetically fixed. Generally, genetic fixation may be accomplished by any standard technique.

Suitable techniques include (1) providing anthers from the progeny of intermated plants and subjecting the anthers to anther culture, or (2) inbreeding the progeny of the intermated plants.

Any suitable anther culture technique which provides double haploid plants can be used. Such techniques are described above (see Dunwell (1985), and Keller et al. (1987), supra).

Inbreeding involves the controlled self-pollination for several generations in order to develop true-breeding or homozygous inbred lines. Inbred lines are derived by a process of self-pollination and selection, usually over 5 or more generations ($S_1$–$S_5$), so that allelic pairs of genes on homologous chromosomes pairs are homozygous or identical.

Plants which have been self-pollinated and selected for type over many generations become homozygous at almost all gene loci and produce a uniform population of true breeding progeny. The degree of inbreeding in a line is approached at the rate of about 50 percent per generation so that by the second generation the plants are about 75 percent homozygous and by the sixth generation the plants are about 98 percent homozygous.

Thereafter, all plants derived from self-pollination, sibling pollination, or random crossing with others in the inbred line theoretically should be essentially genetically identical and, therefor, should be essentially homozygous and uniform in appearance. Consequently, a more specific embodiment of the present invention is the sibling pollination, or random crossing with others in the inbred line of a regenerated plant produced by the anther culture of a hybrid plant of the (H99 ×FR16) ×Pa91 cross.

The inventor has found in maize a particularly important genetic factor, high anther culture (HAC) genetic factor, for enhancing the anther culturability of maize. The HAC genetic factor was created in plants resulting from the three-way cross of (H99 ×FR16) ×Pa91, which experiment is described in the Experimental section below. As discussed therein, seeds containing the HAC genetic factor have been deposited with the American Type Culture Collection (ATCC), in Bethesda, Md.

The HAC genetic factor may be defined using restriction fragment length polymorphism (RFLP) mapping. Any method of analysis which yields the linkage results using any polymorphism can be utilized. The most common methodology at present is to carry out restriction analysis using a given enzyme, perform a Southern hybridization procedure with the desired probe and identify a given RFLP or RFLP's (see, for example in Beckman and Soller, Restriction Fragment Length Polymorphism in Plant Genetic Improvement, In: *Plant Molecular and Cell Biology*, Vol 3, Oxford University Press, 1986, pp. 196–250; and WO 84/04758, the teachings of which are hereby incorporated by reference).

RFLP mapping is directed to a method of hybridization of restriction fragments with labeled probes until a genomic fingerprint of the tested variety is established. A comparison of the genomic fingerprints established with the genomic fingerprints of other individual plants or varieties, which have been established in the same way, determines the degree of relatedness or identity of individuals or varieties. The differences in these genomic fingerprints which define the degree of genetic similarity are restriction fragment polymorphisms. Comparison between the occurrences of a particular characteristic in a variety and the fingerprint of individual isolates by computer analysis will suggest which random clones used as probes are linked to the genes of interest.

An RFLP fingerprint characterizing the genome of 139/39 using 45 public-domain probes is set forth in Table 1, below.

TABLE 1

RFLP Characterization of 139/39

| Probe Designation | Chromosomal Location | Reztriction Enzyme | Molecular Weight in Kb | | |
|---|---|---|---|---|---|
| | | | Fragment 1 | Fragment 2 | Fragment 3 |
| BNL 5.37 | 3L | Hind III | 12.40 | 7.80 | 6.00 |
| BNL 5.40 | 5L | Hind III | 23.00 | 5.60 | |
| BNL 5.47 | 6L/8 | Hind III | 15.90 | 7.90 | |
| BNL 5.71 | 5L | Hind III | 6.50 | 3.10 | |
| BNL 7.65 | 4L | Hind III | 4.40 | 1.60 | |
| BNL 14.28 | 5L/9L | Hind III | 22.90 | | |
| BNL 15.20 | 3L | EcoRI | 12.20 | | |
| NPI 238 (Ceres 7) | 1L | Hind III | 3.40 | | |
| NPI 298 (Ceres 11) | 2L | EcoRI | 7.20 | 4.20 | |
| NPI 446 (Ceres 13) | 3S | Sst I | 18.00 | | |
| NPI 432 (Ceres 15) | 3L | Sst I | 6.70 | 5.50 | 4.90 |
| NPI 386 (Ceres 18) | 4S | Hind III | 23.20 | 22.90 | |
| NPI 396 (Ceres 19) | 3CE/10L | Sst I | 9.30 | | |
| NPI 444 (Ceres 21) | 4L | Hind III | 7.90 | | |
| NPI 409 (Ceres 23) | 5S | EcoRI | 6.60 | | |
| NPI 252 (Ceres 30) | 6L | Hind III | 12.50 | | |
| NPI 280 (Ceres 31) | 6L | Hind III | 7.40 | | |
| NPI 391 (Ceres 33) | 7L | Hind III | 9.40 | 7.60 | |
| NPI 433 (Ceres 36) | 7L | Sst I | 8.60 | 7.90 | |
| NPI 268 (Ceres 39) | 8L | Hind III | 3.40 | | |
| NPI 438 (Ceres 40) | 8L | Sst I | 8.70 | | |
| NPI 211 (Ceres 42) | 9S | Hind III | 8.50 | | |
| BNL 7.13 (Ceres 44) | 9L | EcoRI | 10.10 | | |
| NPI 209 (Ceres 45) | 9L | EcoRI | 15.00 | 5.80 | |
| NPI 264 (Ceres 48) | 10L | Hind III | 11.30 | | |
| NPI 210 (Ceres 57) | 2L | Sst I | 9.10 | 6.60 | |
| NPI 212 (Ceres 58) | 3L | Sst I | 2.70 | | |
| NPI 108 (Ceres 60) | 3L | EcoRI | 10.70 | | |
| NPI 356 (Ceres 61) | 2CE | Sst I | 17.10 | | |
| NPI 262 (Ceres 69) | 1S | Sst I | 10.90 | | |
| NPI 272 (Ceres 73) | 1CE | Hind III | 17.60 | 6.80 | |
| NPI 427/428 (Ceres 78) | 1S/9L | Sst I | 8.40 | 6.60 | |
| NPI 596 (Ceres 91) | 7S | Sst I | 7.90 | | |
| NPI 563 (Ceres 97) | 10L | Hind III | 13.50 | 11.20 | |
| NPI 579 (Ceres 102) | 5S | EcoRI | 13.50 | 3.20 | |
| NPI 270 (Ceres 119) | 4L | Hind III | 10.10 | | |
| NPI 276/364 (Ceres 121) | 3CE/8CE | Sst I | 22.50 | 4.50 | |
| UMC 6 | 2L | EcoRI | 21.30 | | |
| UMC 19 | 4CE | Hind III | 3.80 | | |
| UMC 81 | 9S | Hind III | 10.40 | 8.00 | |
| UMC 90 | 5S | Hind III | 10.40 | 8.00 | |
| UMC 96 | 3L | Hind III | 15.60 | | |
| UMC 126 | 5L | Hind III | 23.10 | 4.50 | |
| UMC 131 | 2CE | EcoRI | 6.10 | | |
| UMC 157 | 1S | EcoRI | 7.70 | | |

It has been determined that the HAC genetic factor (i.e., conditioning in vitro androgenesis) is closely linked to four chromosomal loci in maize (see FIG. 2). Genetic analysis verifies major chromosomal regions having highly significant effects on the androgenetic phentoype are mapped on chromosomes 3 and 9. The two major loci are interactive homozygous recessive chromosomal regions residing on the long arms of chromosomes 3 and 9. Moreover, genetic analysis verifies minor chromosomal regions having effects on the androgenetic phentoype are mapped on chromosomes 1 and 10. The region on chromosome 1, exhibiting the highest response in a heterozygous condition, probably has an independent effect on the response. The region on chromosome 10, exhibiting the highest response in a heterozygous condition, probably has its effect on the trait by interacting with the two major genes affecting the trait. Genes affecting developmental processes at the gametophytic (haploid) level, when examined in a population of microspores, would appear to display additive gene action. The only gene which displayed this type of gene action was on chromosome 10 and its effects are not detectable until after the effects of the other loci are taken into account. On the other hand, the identification of two interacting loci on chromosomes 3 and 9 suggests that these genes are functioning at the sporophytic level.

As seen in FIG. 1, the genomic fingerprint of 139-39 is characterized by a restriction fragment length polymorphism having the following characteristics: the loci on chromosome 1 is detected by a single clone NPI 242 (Ceres 69); the loci on chromosome 3 is bracketed by clones BNL 5.37 and NPI 108 (C60A); the loci on chromosome 9 is bracketed detected by UMC 81 and BNL 7.13 (Ceres 44); and the loci on chromosome 10 is detected by NPI 563 (Ceres 97).

The HAC genetic factor is such that when a series of inbred lines are intermated, the average value of a line can be used to predict the response of a given cross. This is usually a function of additive gene effects and their interaction. This is typical of quantitatively inherited traits in maize (i.e., involving the interaction of more than one gene). Individual hybrids can, however, deviate from the average performance of their parents. Thus, dominance or dominant types of epistasis may also play a role in the anther culture response.

The HAC genetic factor or equivalents thereof can increase the anther culturability of both inbred and heterotic maize plants which possess other desirable characteristics. By "equivalent" is meant to include those genetic factors which are derived from the HAC genetic factor.

A skilled artisan will appreciate that as a result of the inventor's discovery, namely the HAC genetic factor, the source of HAC genetic factor is irrelevant. Any source of DNA which provides a DNA sequence having a homologous segment to the DNA encoding the HAC genetic factor is now readily within the means of those of ordinary skill in the art. A series of probes, made from genes of all or a part of the HAC genetic factor, could be used to find homologous genes or gene segments in unknown plants, particularly maize plants. By "homologous genes or gene segments" is meant to include any DNA sequence whose MRNA hybridizes with the probes of all or a part of the HAC genetic factor, provided that the homologous segment or homologous genes produce a unique phenotype in plants, namely $F_2$ plants or their progeny, plants having an anther frequency response at least 10 percent greater than the anther culture response of the original donor plant.

By "derived" it is also intended to mean DNA sequences, as defined above, modified into altered forms. By "altered" forms is meant to include the addition, deletion, or nonconservative substitution of a limited number of various nucleotides or the conservative substitution of many nucleotides, provided that the proper reading frame is maintained.

Techniques for substitution at predetermined nucleotide sites having a known sequence are well known. Exemplary techniques include site-directed mutagenesis, the polymerase chain reaction technique, and exon shuffling. Substitution may be conducted by making nucleotide insertions, usually on the order of about 1 to about 10 nucleotides, or deletions of about 1 to about 30 nucleotides. Substitutions, deletions, insertions or any subcombination may be combined to arrive at a final construct.

However, as one aspect of the present invention is directed to intermating populations of regenerated plants, the invention is not limited to the exemplary populations deposited at the ATCC, i.e., those individuals which possess the HAC genetic factor. Methods and plants are provided for producing callus cultures, plant tissues, plants and seeds which express culturability and genetically transmit this trait to progeny.

As discussed below, a plant produced according to the present method is capable of transmitting its genetic factor for the expression of the anther culture phenotype to progeny when crossed with a plant of the same species which does not possess the improved anther culture phenotype. The progeny will display an easily defined anther culture response frequency.

Thus, the invention also relates to a plant or plants produced by, i.e. having as an ancestor, a plant containing the HAC genetic factor, as well as variants and mutants thereof. The terms "variants", "modifications", and "mutants" refer to hybrid seed or a plant produced by that hybrid which is phenotypically similar to plants containing the HAC genetic factor.

Use of the HAC genetic factor, however, is preferred because it is stable and capable of being transmitted to progeny over a number of generations. Maize plants containing the HAC genetic factor are characterized by the ability to transmit the HAC genetic factor to progeny when crossed with other maize plants which do not possess the HAC genetic factor.

USES

Research

Improvements by selective breeding have been relatively slow, since only a limited number of generations of plants may be propagated each year. Therefore, relatively minor improvements in plants have been obtained only after years of rigorous work.

The principle of anther culture is to divert the normal development of the male gametophyte by an abnormal pathway, to a sporophytic pathway, resulting in callus and/or embryo formation. Callus and/or embryos are expected to be haploid, carrying the gametic number of chromosomes in the sporophytic phase. This chromosome complement has to be doubled for the regeneration of fertile plants, which then are diploid homozygous.

When in a haploid state, the plant may be transformed by the insertion of the genetic factor which provides improved anther culturability. Thus, when the chromosomes of the haploid plant are doubled, the resulting plant will be homozygous for the genetic factor.

In highly heterozygous, cross-pollinating crops, haploidy creates a rapid method of producing pure breeding lines which can serve as parents in hybrid cultivar development. Production of haploids from $F_1$ donors permits the breeder to effectively select desirable genetic recombinants. Homozygous lines are established through spontaneous chromosome doubling during early stages of invitro culture or through colchicine-induced chromosome doubling of haploids. Because homozygous lines can be made rapidly available, a saving of time of up to 50 percent can be achieved in developing new cultivars.

Another potential application of haploidy is in the production of desirable genetic translocations, substitution and addition lines through the culture of anthers of interspecific and intergeneric hybrids. The production of haploids and thereafter homozygote lines is a significant methodological improvement for selecting rare genotypes, including those with recessive characters, and to include them in new combinations of crossings.

Transfer of Culturability to Other Varieties

The present invention provides a genetically transmitted characteristic which can be selectively incorporated from inbred lines into hybrid breeding programs which will permit production of superior hybrid and inbred lines. An important aim of traditional plant breeding is to engineer improved plants that are valuable as crop plants. Present day genetic engineering techniques are also geared towards similar goals. Anther culture provides a rapid method of inducing homozygosity which is of interest for the production of breeding lines.

Thus, traditional breeding or genetic techniques or a combination of both, may be used to transfer the genetically transmitted characteristic genetic factor to other plants, such as commercially-important lines. Consequently, different strains possessing other genetic factors, or combinations of factors, may be crossed with strains of the same species having improved anther culturability to produce hybrids having increased anther culturability. Such crossing techniques are well-known in the art, and are described in detail above.

In plant breeding, after obtaining a genetically fixed variety having increased anther culturability, it may desirable to use the variety with enhanced anther culturability as a parent in a breeding program. The inventor has found that the present invention provides a genetically transmitted characteristic of anther culturability which can be selectively incorporated in hybrid seed, together with the desirable characteristics of the other parent line.

Any plant containing the genetically transmitted characteristic of anther culturability may be used as a breeding strain for developing other inbreds and hybrids. Conveniently, the transfer of anther culturability is accomplished by pedigree breeding or backcrossing (recurrent selection breeding).

Pedigree breeding starts with the crossing of two genotypes, each of which may have one or more desirable characteristics that is lacking in the other or which complement the other. In the pedigree method, superior $F_2$ plants are selfed and selected in successive generations. In the succeeding generations the heterozygous condition gives way to homogeneous lines as a result of self-pollination and selection (typically in five or more generations). The procedure can be modified by anther culture of the $F_1$, $F_2$, $F_3$, etc. populations.

Backcrossing can be accomplished, for example, by first crossing a superior inbred (recurrent parent) to a donor inbred (non-recurrent parent), which carries the genetically transmitted characteristic of anther culturability. The $F_1$ progeny of this cross is then mated back to the superior recurrent parent followed by selection in the resultant progeny for the desired trait to be transferred from the nonrecurrent parent. After five or more backcross generations with selection for the desired trait, the progeny will be heterozygous for loci controlling the characteristics being transferred, but will be like the superior parent for most or almost all other genes. The procedure can be modified by anther culture of the $F_1$, $F_2$, $F_3$, etc. populations.

After a number of homozygous lines displaying a range of desirable characteristics are produced, experimental hybrids which excel in many or all attributes identified may be produced. After such optimum combinations are determined, the parental lines are increased and large quantities of seedstock are produced by well-known means.

As stated previously, the recombination of anther-derived individuals results in genotypes exhibiting enhanced response to anther culture. Specifically in maize, anther culturable plants are very useful in the development of human food, livestock feed, and as a raw material in industry.

More specifically, the HAC genetic factor can easily be incorporated into proven maize inbreds and hybrids which possess other desirable characteristics, and all subspecies of maize, specifically including the dent corns, the flint corns, the soft or flower corns, the sweet corns, the pod corns, and the pop corns. The inventor has found that hybrids formed from a cross between a parent containing the HAC genetic factor and another parent will have an anther frequency response of approximately the average of the parents' anther frequency response.

The following examples are presented to further illustrate but not limit the scope of this invention. All parts and percentages are by weight unless otherwise indicated.

EXAMPLES

Example 1

Generation of Highly Responsive Germplasm

A. Formation of the Donor Plant

A three-way cross was performed to create the donor plant. The inbred plants used in the three-way cross were H99, FR16, and Pa91. Seed for producing the inbred lines was obtained from Holden's Foundation Seeds, Williamsburg, Iowa (H99 and Pa91) and Illinois Foundation Seeds, Tolono, Ill. (FR16). All lines were maintained by controlled self-pollination for two years prior to being used for crossing. The three-way cross, (H99 × FR16) × Pa91 was made by controlled pollination essentially following the procedures set forth in Hallauer (1987), described above.

Donor plants were field-grown during April to August, 1985 in Champaign, Ill. Tassels with anthers containing microspores at the late uninucleate-early binucleate state of development, as determined microscopically after treatment with acetocarmine, were removed from donor plants prior to emergence from the whorl. Tassels were then wrapped in moist paper towels, covered with aluminum foil, and maintained at 8° C. for 14 days. Before anther excision, tassels were surface sterilized for 15 minutes in a 0.5 percent sodium hypochlorite solution followed by a sterile water rinse. Only anthers from the central portion of the main tassel branch were used.

B. Anther Culture

Sixty anthers were placed in a 20×60 mm Petri dish containing 20 ml of medium. The medium consisted of YP basal salts (see Ku et al., 1978, supra) with the addition of 5.0 g/l activated charcoal, 500 mg/l casein hydrolysate, 0.1 mg.l 2,3,4,5-triiodobenzoic acid, 120 g/l sucrose, and 8.0 g/i agar (Gibco) adjusted to pH 5.8. Typically 3-6 dishes were obtained from each tassel harvested. Dishes containing freshly plated anthers were sealed with Parafilm and placed in plastic boxes covered with aluminum foil.

After one week in the dark at 28° C., dishes were transferred to clear boxes and grown under cool white florescent lights (60 umol/m/sec) with a 16 hour photoperiod. Between 4 and 6 weeks later, anthers with recognizable embryo-like structures were apparent.

Embryo-like structures were yellowish-white and globular in appearance and resembled zygotic embryos displaying varying degrees of abnormal tissue proliferation. Anther response frequency could be expressed as the total number of embryo-like structures produced per 100 anthers cultured.

Embryo-like structures were lifted from the anthers and placed onto a regeneration medium (YP with 1.0 mg/l indole-3-acetic acid), 1.0 mg/l kinetin, 146 mg/l glutamine, and 30 g/l sucrose). After 2-3 weeks, plantlets were placed on a hormone-free medium (YP salts only) and, after root formation, transferred to soil and grown to maturity in the greenhouse.

Two anther culture-derived embryo-like structures, obtained from two separate tassels, regenerated plants which were grown to maturity during October to December, 1985. One plant (#139) produced an ear shoot and a tassel with no anther extrusion. A second plant (#39) produced viable pollen but the ear shoot was late in development. The pollen from plant #39 was applied to plant #139 resulting in the formation of a single $F_1$ hybrid (139/39) seed.

The $F_1$ hybrid seed was germinated and the resulting plant was self-pollinated, i.e., pollen from one plant is used to fertilize itself to produce and $F_2$ ($S_0$) population.

C. Genetic Fixation of Segregating Population

Self-Pollination of $F_2$ Plants

The $F_2$ population was grown in the field in Champaign, Ill. during the summer of 1986 and fourteen plants were self-pollinated and grown ear-to-row.

The resulting fourteen $S_1$ inbreds were evaluated for their anther culturability. Evaluation was conducted by selecting tassels with anthers containing late uninucleate-early binucleate microspores, as determined by mithramycin/floureseent staining as set forth in Pace et al., (1987), "*Anther Culture of maize and the visualization of embryogenic microspores by flourescent microscopy*", Theor. Appl. Genet., 73:863-869, the procedures of which are incorporated by reference. Selected tassels were removed from the donor plants prior to emergence from the whorl. The results are set forth in Table 2.

TABLE 2

| Mean Anther Culture Response from Cultured Anthers of 14 $S_1$ Families of Maize | | |
|---|---|---|
| Genotype | Anthers Cultured | ELS+ Produced (per 100 Anthers) |
| 139/39-01 | 900 | 275.1 |
| 139/39-02 | 900 | 269.2 |
| 139/39-03 | 900 | 134.2 |
| 139/39-04 | 900 | 126.0 |
| 139/39-05 | 900 | 238.4 |
| 139/39-06 | 900 | 64.2 |
| 139/39-07 | 900 | 79.8 |
| 139/39-08 | 900 | 30.4 |
| 139/39-09 | 900 | 248.0 |
| 139/39-10 | 900 | 57.6 |
| 139/39-11 | 900 | 130.0 |
| 139/39-12 | 900 | 87.5 |
| 139/39-13 | 900 | 70.9 |
| 139/39-14 | 900 | 119.8 |

+Embryo-Like Structures
Means for the 14 $S_1$ isolates ranged from 9.2% and 41.3%.

A population of $S_1$ seed (ATCC Nos. 40519 and 40520) containing an approximate equal distribution of 139/30-01 to 139/39-14 (hereinafter "139/39-bulk") was deposited at and issued accession number from the ATCC, 212301 Parklawn Drive, Rockville, Md. 20852-1176 on Dec. 1, 1988; a supplemental deposit pursuant to the United States Patent Office Rules for the Deposit of Biological Materials was made on Dec. 1, 1989.

A distribution of response frequencies from individual plants from the three-way cross, (H99 ×FR16) ×Pa91, is presented in FIG. 1A.

As can be seen in FIG. 1A, the response frequencies are skewed toward the lower values and the overall mean response is 3.5 percent. Only 4 of the 53 (7.5 percent) plants displayed anther-culture response frequencies greater than 10 percent.

Figure 1B:
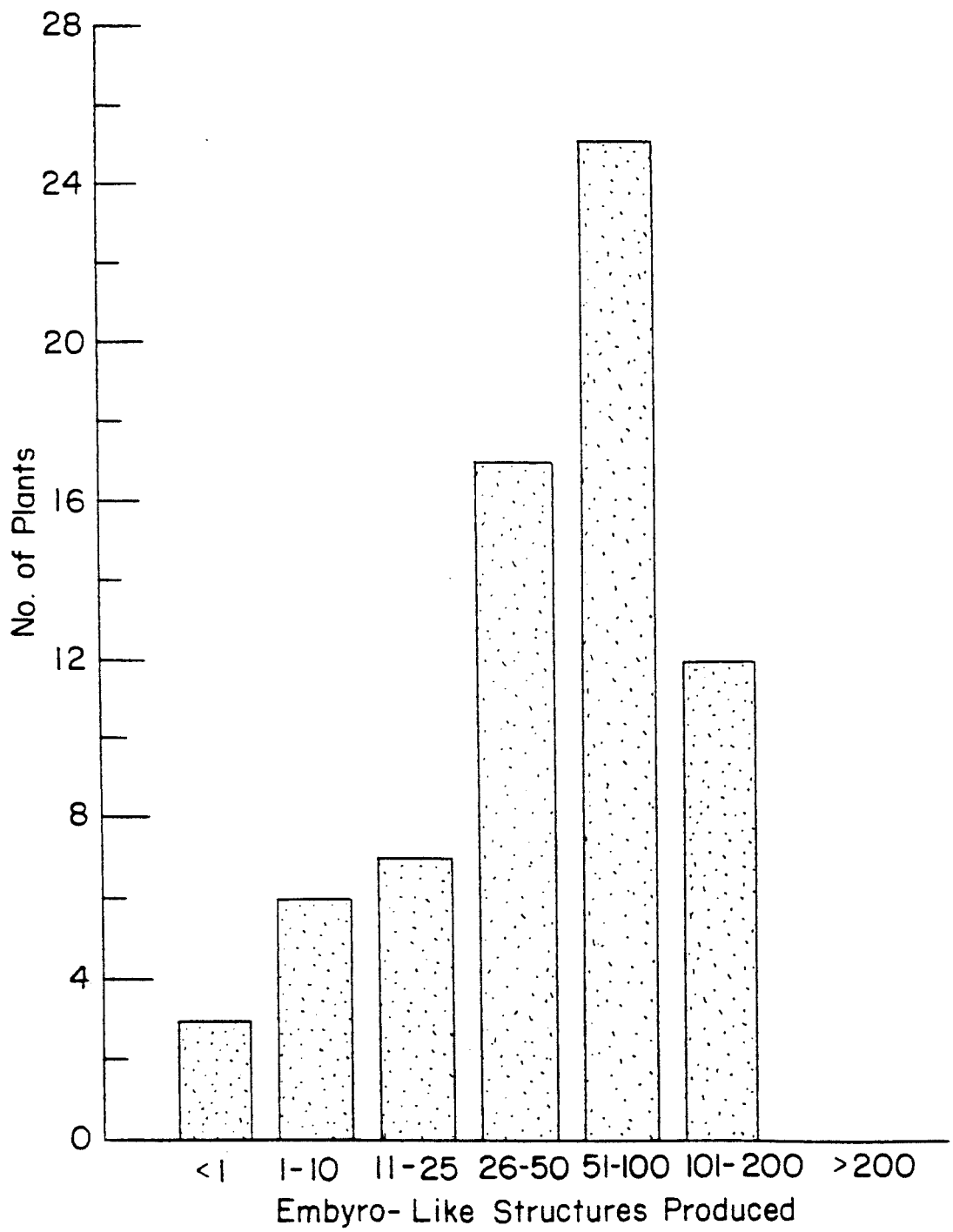
FIG. 1B illustrates the frequency distribution of anther culture response from individual maize plants: 145, families (n−70).

Individual anther culture response frequencies of the $S_1$ plants are presented in FIG. 1B.

As can be seen in FIG. 1B, a dramatic shift toward increased anther response was observed. The overall mean response frequency for the $S_1$ plants was 23.4 percent. A total of 54 of the 70 (77.1 percent) $S_1$ plants evaluated had response frequencies greater than 10 percent.

A single cycle of selection resulted in greater than a six-fold increase over the original three-way cross in anther culture responsiveness as measured by the percentage of anthers producing embryo-like structures.

The two original plants from which the tassels were harvested (FIG. 1a), that ultimately lead to the regeneration of plants #39 and #139, were not among the most productive based on their individual anther response (0.8 percent and 4.4 percent, respectively). However, the intermating of microspore-derived plants appears to be an effective means of shifting allelic frequencies toward increased responsiveness.

Anther Culture of $F_2$ Plants

Individuals of 139/39-05 were subjected to the anther culture technique set forth in step B, above. Seed from the resulting regenerated plants, 139/39-DH (ATCC number 40520). 139/39-DH (ATCC 40520) was deposited at and issued an accession number from the ATCC, 212301 Parklawn Drive, Rockville, Md. 20852-1176 on Dec. 1, 1988; a supplemental deposit pursuant to the United States Patent Office Rules for the Deposit of Biological Materials was made on Nov. 2, 1990.

Self-Pollination of S$_2$ Plants

Self-pollinations were made with 4 of the most responsive families and S$_2$ seed from the resulting ears were grown during April to October, 1988. Self-pollinations were made within each of the families to produce novel S$_3$ germplasm of this invention.

Since this material has undergone forced inbreeding for 4 generations (F$_1$, F$_2$ (S$_0$), S$_1$, S$_2$) approximately 95 percent of those loci which were heterozygous in the original F$_1$ hybrid are now homozygous.

Example 2

Transfer of Culturability to Other Inbred Genotypes

Crosses were made between the four selected S$_2$ families and four other commercially-important inbred genotypes (LH38, LH51, LH82, and LH123 obtained from Holden's Foundation Seeds, Williamsburg, Iowa) each of which is relatively non-responsive to anther culture.

The resulting F$_1$ hybrids were evaluated for their anther culturability as measured by embryo-like structure formation. The results are set forth in Table 3.

TABLE 3

| Mean Anther Culture Response of 16 F$_1$ hybrids of Maize | | |
|---|---|---|
| Cross | Anthers Cultured | ELS Produced (per 100 Anthers) |
| 139/39-01 × LH51 | 6,240 | 30.7 |
| 139/39-02 × LH51 | 6,360 | 67.4 |
| 139/39-05 × LH51 | 6,420 | 18.6 |
| 139/39-09 × LH51 | 7,320 | 47.3 |
| LH123 × 139/39-01 | 6,660 | 48.8 |
| LH123 × 139/39-02 | 7,680 | 171.1 |
| LH123 × 139/39-05 | 7,560 | 107.6 |
| LH123 × 139/39-09 | 7,800 | 104.2 |
| 139/39-01 × LH82 | 6,300 | 20.6 |
| 139/39-02 × LH82 | 6,600 | 29.1 |
| 139/39-05 × LH82 | 6,600 | 6.2 |
| 139/39-09 × LH82 | 6,720 | 32.5 |
| 139/39-01 × LH38 | 6,840 | 5.7 |
| 139/39-02 × LH38 | 6,900 | 29.2 |
| 139/39-05 × LH38 | 5,880 | 17.7 |
| 139/39-09 × LH38 | 7,440 | 5.3 |

As can be seen from the above table, anther culture response frequencies ranged from 5.7 to 171.1 embryo-like structures produced per 100 anthers cultured. This demonstrates that the HAC genetic factor is effective in improving the anther culture response in otherwise unresponsive germplasm.

Example 3

Selection of HAC loci using Anther Culture

Pollen from 139/39-bulk (ATCC 40519) was applied to silks of the non-responsive inbred line, UP25 and F$_1$ seed was harvested. The resulting F$_1$ seed was planted to generate donor plants which were anther cultured as described in the Example 1.

Anther derived double haploids were recovered and crossed back to UP25. The resulting BC$_1$ seed was planted to generate donor plants for another round of anther culture. Eleven BC$_2$ progeny were produced from the cross of 139/39 and UP25. Anther culture was carried out on the F$_1$ and BC$_1$ generations. Doubled haploids resulting from the anther culture process were used to continue the backcross procedure. In the UP25 backcross series the expected frequency of the 139/39 allele is 12.5%, since they should be 87.5% the recurrent parent (UP25) after 2 backcrosses. For example, if between 1 and 3 of the 11 backcross progeny retain the allele, there is no significant deviation from the expected result. However, if 4 of the progeny retain the allele this is a significant deviation from the expected value (0.05 level). When 5 or 6 of the progeny retain the allele the significance level increases to the 0.001 level. Five of the loci identified as bracketing the genes conditioning androgenic response in 139/39 detected a polymorphism between 139/39 and UP25: BNL 22, Ceres 69 UMC 81, Ceres 60 and Ceres 44. Of the 11 BC$_2$ progeny, 3 retained the 139/39 allele of BNL 22. Four of the 11 progeny retained the 139/39 allele at Ceres 69 and UMC 81. Five of the 11 progeny carried to 139/39 allele for Ceres 60 and 6 did so for Ceres 44.

The results of such analysis are set forth in Table 3. The data supports the conclusion that selection during backcrossing (i.e., the anther culture process itself) causes the preferential retention of the 139/39 allele at all loci conditioning high anther culture response for which the parents carried different alleles.

Other variations will be evident to those skilled in the art. Therefore, the scope of the invention is intended to be defined by the claims.

The present invention is not to be limited in scope by the cell line or seeds deposited, since the deposited embodiments are intended as single illustrations of one aspect of the invention and any cell lines or seeds which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

What is claimed is:

1. A method for the production of a maize plant having improved anther culturability, the steps of the method comprising (a) providing anthers from at least one heterozygous donor maize plant having the ability to be anther cultured, (b) regenerating, from anthers obtained from the donor plant, at least two microspore-derived parent plants capable of being intermated, (c) intermating the regenerated plants to produce an F$_1$ population, and (d) self-pollinating or cross-pollinating individuals of the F$_1$ population to generate at least one F$_2$ population having a mean frequency response of at least 10% greater than the anther frequency response of any parent, wherein individual plants of said F$_2$ population have a genome identified by the following restriction fragment length polymorphism: a band of about 10.8 kb when digested with restriction enzyme EcoRI and probed with Ceres 60 probe and a band of about 17.0 kb when digested with restriction enzyme SstI and probed with Ceres 135.

2. The method of claim 1, wherein the donor plant is derived from the group consisting of plants occurring from open pollination; wild relatives of inbred lines; mutations of inbred lines; transformed inbred lines; and the progeny of crosses of inbred lines.

3. The method of claim 2 wherein the donor plant is obtained from progeny of inbred lines are obtained from the group consisting of single crosses, three-way crosses, and double crosses.

4. The method of claim 3, wherein the donor plant is obtained from a three-way cross of (H99×FR16)×pa91.

5. The method of claim 1, wherein step (c) comprises randomly intermating the regenerated plants by singlet three-way or double crosses.

6. The method of claim 1, wherein step (d) comprises self pollinating individuals of the $F_1$ population.

7. The method of claim 1, wherein the $F_2$ population produced in step (d) has a segregating population which is fixed genetically by a method selected from the group consisting of selfing, and anther culture techniques.

8. A maize plant regenerated from the method of claim 7 in which said plant has an anther culture frequency response of at least 10% greater than the frequency response of any parent and a genome identified by the following restriction fragment length polymorphism: a band of about 10.8 kg when digested with restriction enzyme EcoRI and probed with Ceres 60 probe and a band of about 17.0 kb when digested with restriction enzyme SstI and probed with Ceres 135.

9. A maize plant produced by intermating the plant of claim 8 with a second maize plant wherein the progeny of said intermating retains the traits of improved anther culturability.

* * * * *